(12) United States Patent
Gayet et al.

(10) Patent No.: US 10,017,444 B2
(45) Date of Patent: Jul. 10, 2018

(54) METHOD FOR THE PURIFICATION OF NATURAL VANILLIN

(71) Applicant: Rhodia Operations, Paris (FR)

(72) Inventors: Hubert Gayet, Saint-Priest (FR); Denis Revelant, Genas (FR); Martine Vibert, Lyons (FR)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 15/480,068

(22) Filed: Apr. 5, 2017

(65) Prior Publication Data

US 2017/0204039 A1 Jul. 20, 2017

Related U.S. Application Data

(63) Continuation of application No. 14/762,384, filed as application No. PCT/EP2014/051023 on Jan. 20, 2014, now Pat. No. 9,617,198.

(30) Foreign Application Priority Data

Jan. 24, 2013 (FR) ...................................... 13 50617
Dec. 23, 2013 (FR) ...................................... 13 63444

(51) Int. Cl.
*C07C 45/87* (2006.01)
*C07C 47/58* (2006.01)
*B01D 3/00* (2006.01)

(52) U.S. Cl.
CPC ................... *C07C 47/58* (2013.01)

(58) Field of Classification Search
CPC ......... C07C 45/82; C07C 47/58; B01D 3/141; B01D 3/143
USPC ....................... 568/442; 202/158; 203/80, 91
See application file for complete search history.

(56) References Cited

U.S. PATENT DOCUMENTS

| | | | |
|---|---|---|---|
| 2,187,366 A | 1/1940 | Schulz | |
| 2,745,796 A | 5/1956 | Toppel | |
| 4,075,248 A | 2/1978 | Marshall et al. | |
| 5,017,388 A | 5/1991 | Rabenhorst et al. | |
| 5,128,253 A | 7/1992 | Labuda et al. | |
| 5,262,315 A | 11/1993 | Gross et al. | |
| 6,133,003 A * | 10/2000 | Rabenhorst | C12P 7/24 426/44 |
| 6,235,507 B1 * | 5/2001 | Muheim | C12P 7/24 435/123 |
| 6,844,019 B1 * | 1/2005 | Cheetham | C12P 7/42 426/534 |

FOREIGN PATENT DOCUMENTS

| | | |
|---|---|---|
| CA | 1121384 A | 4/1982 |
| CN | 1887839 A | 1/2007 |
| CN | 101234958 A | 8/2008 |
| CN | 102276434 A | 12/2011 |
| JP | S39-26838 B | 11/1964 |
| JP | S55-79337 A | 6/1980 |
| JP | H03-30683 A | 2/1991 |
| JP | H05-227980 A | 9/1993 |
| JP | H05-244965 A | 9/1993 |

OTHER PUBLICATIONS

Converti et al. Microbial Production of Biovanillin. Brazilian Journal of Microbiology, 2010, vol. 41: 519-530.*
Böddeker et al; "Pervaporation at the vapor pressure limit: Vanillin", Journal of Membrane Science, 137, (1997), 155-158 (4 pages).
Office Action issued in Japanese Application No. 2015-554116; dated Aug. 1, 2017 (22 pages).

* cited by examiner

*Primary Examiner* — Sikarl A Witherspoon
(74) *Attorney, Agent, or Firm* — Osha Liang LLP

(57) ABSTRACT

The invention relates to a natural vanillin, which is in the form of an amorphous solid of which the color, in ethanolic solution at 10% by weight, is less than or equal to 200 Hazen, preferably less than or equal to 100 Hazen.

20 Claims, 1 Drawing Sheet

METHOD FOR THE PURIFICATION OF NATURAL VANILLIN

This application is a divisional of U.S. patent application Ser. No. 14/762,384, filed Sep. 2, 2015, now U.S. Pat. No. 9,617,198; which is National Stage Entry of PCT/EP2014/051023, filed Jan. 20, 2014; the entire contents of each of which are incorporated herein by reference.

The present invention relates to a process for purifying natural vanillin. The invention also relates to the natural vanillin that can be obtained by means of the process according to the invention and to a facility for producing purified natural vanillin.

Vanillin can be obtained via two distinct routes:
- a "natural" route based on a biotechnological process, comprising in particular the culturing of a microorganism (fungi, bacteria, etc.) capable of enabling the bioconversion of a fermentation substrate into vanillin. Such a process in which the fermentation substrate is ferulic acid is in particular known from EP 0 885 968 and EP 0 781 817. This process results in the production of a vanillin termed natural vanillin;
- a "synthetic" route comprising conventional chemical reactions starting from guaiacol, not involving a microorganism. This process results in the production of a vanillin termed synthetic vanillin.

Currently, natural vanillin, obtained via the "natural" route, is purified by extraction with a solvent, followed by crystallization. This process results in a vanillin at specification limit: medium purity, colored, and at a yield of about 90%. The crystallization step has the drawback of requiring the use of organic solvents. The use of such solvents, although authorized, can present drawbacks from a toxicological and/or environmental point of view.

As it happens, currently, no one is capable of providing a process for purifying natural vanillin which does not require the use of crystallization organic solvent.

Processes for purifying synthetic vanillin by distillation are known. However, the streams at the end of the process for producing vanillin via the natural route or via the synthetic route are quite distinct. The stream at the output of the process for preparing natural vanillin typically comprises natural vanillin, vanillyl alcohol and a solvent, preferably a food-grade solvent, for example ethyl acetate. This stream may also comprise vanillic acid, ferulic acid, guaiacol, benzoic acid, dimers and trimers, guaiacol derivatives and water. The stream at the output of the process for preparing synthetic vanillin typically comprises synthetic vanillin, ortho-vanillin, trimers, guaiacol and DFG (diformaldehyde guaiacol). The way in which these various streams are apprehended is therefore distinct.

One objective of the present invention is therefore to provide a process for purifying natural vanillin, in particular not requiring the use of solvent.

Another objective of the present invention is to provide a process for purifying natural vanillin which is simple to carry out and which can be carried out continuously so as to be compatible with industrial processes. In particular, the present invention seeks the provision of a process for purifying natural vanillin which results in a yield greater than 90%, preferably greater than 95%.

Yet another objective of the present invention is to provide an adjustable process for purifying natural vanillin which makes it possible to obtain, according to the desired specifications:
- a very pure natural vanillin, for example having a purity greater or equal to 99%; or
- a natural vanillin of lower purity, for example having a purity of 96% to 98.9%, and having, by virtue of the presence of certain impurities, organoleptic properties different than those of the very pure natural vanillin and which are close to the organoleptic properties of vanilla pod. The process according to the invention therefore advantageously makes it possible to control the level of residual impurities and in particular those which have a positive influence on the organoleptic quality of the final natural vanillin.

Since natural vanillin is a heat-sensitive product (in particular formation of trimers by heating vanillin), another objective of the present invention is to provide a purification process which preserves all the properties of vanillin.

It would also be advantageous to provide a process for purifying natural vanillin which is more environmentally friendly and which makes it possible to obtain a very pure and very weakly colored natural vanillin without degradation of its properties.

Yet other objectives will become apparent on reading the description of the invention that follows.

The natural vanillin according to the invention, and obtained by means of the process of the invention, is a natural flavoring substance according to article 9.2.c) of EC regulation 1334/2008. That is to say it is a flavoring substance obtained by physical, enzymatic or microbiological processes from materials of plant, animal or microbiological origin taken as they are or after conversion thereof for human consumption by one or more of the conventional processes for preparing food products. A natural flavoring substance corresponds to a substance which is naturally present and has been identified in the natural environment.

The invention therefore relates to a process for purifying natural vanillin, comprising at least one step in which natural vanillin is evaporated.

The applicant has discovered, surprisingly, that a novel process for purifying natural vanillin makes it possible to obtain a product having a purity greater than or equal to 99% by weight and having a color less than or equal to 200 Hazen in ethanol solution at 10% by weight.

This process makes it possible, in particular when it is applied to a starting natural vanillin having a degree of purity ranging from 95% to 99% by weight, to obtain a very weakly colored vanillin with a yield greater than or equal to 95% by weight relative to the initial amount of vanillin present in the starting product.

In the context of the present invention, the term "process for producing natural vanillin" is intended to mean processes for preparing vanillin via biotechnological routes. Such processes comprise in particular the culturing of a microorganism capable of enabling the bioconversion of a fermentation substrate into vanillin. Such a process in which the fermentation substrate is ferulic acid is M particular known from EP 0 885 968 and EP 0 761 817.

In the context of the present invention, the term "natural vanillin" is intended to mean the vanillin obtained by means of preparation processes as defined above.

In the context of the present invention, the term "ultralight impurities" or "ultralights" is intended to mean compounds of which the volatility is higher than that of natural vanillin under the pressure and temperature conditions under consideration. The ratio between the vapor pressure of the ultralights and the vapor pressure of vanillin is between 60 and 200 at 134° C. (or at the distillation temperature). Among the ultralight impurities, mention may be made of ethyl acetate.

The term "light impurities" or "lights" is intended to mean compounds of which the relative volatility is intermediate between that of the ultralights and that of natural vanillin under the pressure and temperature conditions under consideration. Among the light impurities, mention may be made of benzoic add and guaiacol.

The term "heavy impurities" or "heavies" is intended to mean compounds of which the relative volatility is lower than that of natural vanillin under the pressure and temperature conditions under consideration. The ratio between the vapor pressure of the heavies and the vapor pressure of vanillin is between 0.3 and 0.7 at 150° C. (or at the distillation temperature). Among the heavy impurities, mention may be made of dimers and trimers of vanillin (i.e. compounds with a backbone having two, respectively three, phenyl groups, the dimers being advantageously selected from diphenylmethanes), vanillyl alcohol, vanillic acid, ferulic acid, benzoates, in particular sodium benzoate, and guaiacol derivatives, for example 4-methyl guaiacol and 4-ethyl guaiacol.

Generally, the volatility is the capacity of a substance to vaporize.

In a first aspect, the present invention relates to a process for purifying a stream resulting from a process for producing natural vanillin, said stream comprising natural vanillin and at least vanillyl alcohol, by distillation enabling the separation of the natural vanillin from the vanillyl alcohol.

At the end of the process for preparing natural vanillin, a liquid stream (F1) comprising the natural vanillin, the ultralights, the lights and the heavies is obtained. In one particular embodiment, the ultralights represent from 50% to 90% by weight of the stream (F1), the lights represent from 0.1% to 10% by weight of the stream (F1), the heavies represent from 0.1% to 15% by weight of the stream (F1), and the natural vanillin represents from 5% to 35% by weight of the stream (F1). Preferably, the ultralights represent from 60% to 80% by weight of the stream (F1), the lights represent from 0.5% to 5% by weight of the stream (F1), the heavies represent from 1% to 10% by weight of the stream (F1), and the natural vanillin represents from 10% to 30% by weight of the stream (F1).

The starting composition of the stream (F1) is given by way of indication, and the process of the invention is also suitable for mixtures comprising more or less natural vanillin.

In one particular embodiment, the stream (F1) comprises:
from 5% to 35% by weight of natural vanillin, in particular from 10% to 30% by weight;
from 0.05% to 10% by weight of vanillyl alcohol, in particular from 0.1% to 5% by weight;
from 0.0% to 2% by weight of vanillic acid, in particular from 0.01% to 0.6% by weight;
from 0.0% to 2% by weight of ferulic acid, in particular from 0.01% to 0.9% by weight;
from 0.0% to 2% by weight of guaiacol, in particular from 0.01% to 0.6% by weight;
from 0.0% to 5% by weight of dimers and of trimers, preferably from 0.05% to 5% by weight of dinners and of trimers, in particular from 0.1% to 5% by weight; the dimers and trimers being compounds with a backbone having respectively two or three phenyl groups, the dimers being advantageously selected from diphenylmethanes;
from 0.0% to 5% by weight of various organic compounds likewise biosynthesized (for instance 4-methyl guaiacol, 4-ethyl guaiacol and/or 4-vinyl guaiacol), preferably from 0.01% to 5% by weight, in particular from 0.05% to 1% by weight;
from 0.0% to 10% by weight of benzoic acid, preferably from 0.01% to 10% by weight of benzoic acid, in particular from 0.05% to 5% by weight;
from 0.0% to 5% by weight of water, preferably from 0.01% to 5% by weight of water, in particular from 0.05% to 3% by weight;
the remainder to 100% by weight being a food-grade solvent, for example ethyl acetate.

Preferably, the operating pressure during distillation is between 2 and 10 mbar, preferably between 3 and 6 mbar; for example it is 4 mbar.

In the context of the present invention, the term "operating pressure" is intended to mean the pressure at the top of the distillation column.

Advantageously, the pressure drop in the distillation column must be as small as possible. Preferably, the pressure drop is between 1 and 10 mbar, preferably between 2 and 8 mbar; for example it is 3 or 4 mbar.

In the context of the present invention, and unless otherwise indicated, the expression "between x and y" includes the values x and y. In the context of the invention, this expression also means "from x to y".

In the process according to the invention, one or more distillation columns are used.

Preferably, the distillation column(s) comprise(s) from 7 to 40 theoretical plates, preferably from 12 to 30 theoretical plates.

Advantageously, the process according to the invention makes it possible to obtain a natural vanillin having a purity greater than or equal to 96%, preferably greater than or equal to 98%.

In one embodiment, the process according to the invention makes it possible to obtain a very pure natural vanillin, in particular having a purity greater than or equal to 99% and preferably containing less than 1000 ppm of vanillyl alcohol. This embodiment can be obtained by adjusting the distillation parameters.

In another embodiment, the process according to the invention makes it possible to obtain a natural vanillin of lower purity, for example having a purity of 96% to 98.9% and comprising impurities which give the stream of natural vanillin obtained organoleptic properties which are different than those of the very pure natural vanillin and close to those of the vanilla pod. In this embodiment, the final stream of natural vanillin may comprise up to 3% by weight of impurities. Among the impurities are, in the majority, vanillyl alcohol, and the dimers and/or trimers, in particular diphenylmethanes, which can represent up to 1% by weight of the stream, and in the minority, vanillic acid, guaiacol, benzoic acid and biosynthesized organic compounds, which may each be present at up to 500 ppm in the stream. This embodiment can be obtained by adjusting the distillation parameters.

In the context of the process of the invention, a vanillin trimerization chemical reaction may occur, which affects the vanillin yield.

The process for purifying natural vanillin by distillation according to the present invention can be carried out in a different manner:
by batch distillation;
by continuous distillation; or
by continuous distillation on a divided wail column (DWC).

Batch Distillation

In one embodiment, the process according to the invention is carried out by batch distillation. The process thus comprises various unitary distillation operations making it possible to distinctly separate the ultralights, the lights, the vanillin and the heavies.

In the batch process, the stream (F1) is charged to a distillation column. The process makes it possible to recover:
- in a first fraction, the ultralights;
- in a second fraction, the lights which may optionally comprise natural vanillin at a low concentration;
- in a third fraction, the stream comprising the natural vanillin; and
- in the distillation concentrate, the heavies which may optionally comprise natural vanillin at a low concentration.

In this embodiment, the term "low concentration" is intended to mean a concentration preferably of at most 10%, preferably of at most 5%, for example of at most 3% by weight relative to the total weight of the fraction.

The first, second and third fractions can advantageously be recovered by condensation using conventional devices known to those skilled in the art.

Those skilled in the art are perfectly capable of setting the distillation parameters, such as in particular the column diameter, the column height and the packing. The following will simply be mentioned. The size (in particular the diameter) of the distillation columns depends on the stream circulating and on the internal pressure. They will therefore be sized mainly according to the flow rate of mixture to be treated. It will be specified that the column can be packed without distinction with plates or with stacked or woven packing, as is fully known to those skilled in the art. Once the facility has been determined, those skilled in the art adjust the operating parameters of the column.

Preferably, the distillation column comprises from 7 to 30 theoretical plates, preferably from 5 to 15 theoretical plates, for example 7 to 10 theoretical plates.

Preferably, the packing of the column is a woven packing with a surface area of 400 to 600 $m^2/m^3$.

This distillation process makes it possible to obtain the natural vanillin with a yield of 90% to 95%, preferably of 90% to 93%.

In one embodiment, the process according to the invention makes it possible to obtain a very pure natural vanillin, in particular having a purity greater than or equal to 99% and preferably containing less than 1000 ppm of vanillyl alcohol.

In another embodiment, the process according to the invention makes it possible to obtain a natural vanillin of lower purity, for example having a purity of 96% to 98.9% and comprising impurities which give the stream of natural vanillin obtained organoleptic properties which are different than those of the very pure natural vanillin and close to those of the vanilla pod. In this embodiment, the final stream of natural vanillin may comprise up to 3% by weight of impurities. Among the impurities are, in the majority, vanillyl alcohol, and the dialers and/or trimers, in particular diphenylmethanes, which can represent up to 1% by weight of the stream, and in the minority, vanillic acid, guaiacol, benzoic acid and biosynthesized organic compounds, which may each be present at up to 500 ppm in the stream.

Continuous Distillation

In one embodiment, the process according to the invention is carried out by continuous distillation.

Topping/Tailing

In one particular embodiment, the process carried out by continuous distillation comprises the following steps:
a) in a first step, the stream (F1) is treated in order to remove the ultralights (stream (F11)) that it contains and more particularly the ethyl acetate; the resulting stream comprising the natural vanillin, the lights and the heavies is called stream (F2);
b) in a second step, the stream (F2) is fed into a first distillation column, making it possible to recover, at the top of the distillation, a stream (F12) comprising the lights and which may optionally comprise a low concentration of natural vanillin, and at the bottom of the distillation, a stream (F13) comprising the natural vanillin and the heavies and which may optionally comprise a low concentration of lights;
c) the stream (F13) is continuously fed into a second distillation column, making it possible to recover, at the top of the distillation, a stream (F14) comprising the natural vanillin, and at the bottom of the distillation, a stream (F15) comprising the heavies and optionally a low concentration of natural vanillin.

Those skilled in the art are perfectly capable of setting the distillation parameters, such as in particular the column diameter, the column height and the packing. The following will simply be mentioned. The size (in particular the diameter) of the distillation columns depends on the stream circulating and on the internal pressure. They will therefore be sized mainly according to the flow rate of mixture to be treated. It will be specified that the column can be packed without distinction with plates or with stacked or woven packing, as is fully known to those skilled in the art. Once the facility has been determined, those skilled in the art adjust the operating parameters of the column.

In this embodiment, the term "low concentration" is intended to mean a concentration preferably of at most 5%, preferably of at most 3%, for example of at most 2% by weight relative to the total weight of the fraction.

According to one preferred embodiment of the topping/tailing scheme, at least one part of the stream (F15) is mixed with the stream (F14) so as to be able to vary the final composition of a stream of purified natural vanillin.

Preferably, the stream (F12) at the top of the distillation in step b) comprises the lights, and in particular benzoic acid and guaiacol and optionally a low concentration of natural vanillin.

Preferably, the distillation column of step b) comprises from 20 to 35 theoretical plates, preferably from 23 to 30 theoretical plates. The distillation column of step b) comprises in particular from 8 to 15 theoretical plates for the concentration section and from 12 to 20 theoretical plates for the depletion section, preferably from 10 to 13 theoretical plates for the concentration section and from 13 to 17 theoretical plates for the depletion section, The distillation column of step b) may be a distillation column equipped with stacked packing with a height of from 2×2600 mm to 2×3000 mm (2600 mm to 3000 mm for each of the concentration and depletion sections). The packing of the column is preferably woven packing owing to the very low processing pressures.

In the column of step b), the operating pressure is preferably between 2 mbar and 10 mbar, preferably between 3 mbar and 6 mbar. The pressure drop is preferably from 1 to 10 mbar and preferably from 1 to 8 mbar. During step b), the reflux ratio is between 10 and 30, preferably between 15 and 25.

The reflux ratio is defined as the ratio of the flow rate of material reinjected from the top of the column to the inside of the column (i.e. the reflux flow rate) to the flow rate actually exiting at the outlet of the top of the column.

The stream (F2) feed point is selected in a manner known to those skilled in the art; it is in particular selected in such a way as to avoid back-mixing. Preferably, the feed point is at the top of the depletion section.

The ratio of the distillation flow rate (flow rate of the stream (F12)) to the feed flow rate (flow rate of the stream (F2)) is preferably from 0.05 to 0.5.

The reflux flow rate is preferably from 1.4 to 3 times the feed flow rate; for example, it is twice the feed flow rate.

Preferably, during step b), the temperature at the bottom of the column is between 100° C. and 160° C., particular between 120° C. and 150° C. Preferably, during step b), the temperature at the top of the column is between 80° C. and 120° C., preferably between 90° C. and 110° C.

The residence time of the vanillin at the bottom of the column of step b) is between 30 minutes and 5 hours; it is for example 3 hours.

The distillation is initiated by adjusting the flow rate of stream (F12) so as to maintain an approximate temperature of preferably from 100 to 160° C. The temperature difference between the top (vapor temperature) and the bottom (temperature of the liquid) is preferably between 35 and 45° C.

In order to perform the distillation of step b), heat can be supplied to the bottom of the column in particular by a falling-film or scraped-film boiler, by a shell-and-tube heat exchanger heated with steam or by a heat-transfer fluid, by means of heating coils fed with steam or by a heat-transfer fluid or by any other equivalent device, preferably by a heat-transfer fluid. Preferably, the energy for the distillation is supplied by a boiler of falling-film type, a forced-circulation shell-and-tube device or a themosiphon shell-and-tube device.

The stream (F13) at the bottom of the column at the end of step b) is sent to the distillation column of step c), also called tailing column.

Preferably, the column of step c) comprises from 10 to 30 theoretical plates, preferably from 15 to 25 theoretical plates. The distillation column of step c) comprises in particular from 4 to 14 theoretical plates for the depletion section and from 6 to 16 theoretical plates for the concentration section.

Preferably, the column of step c) is equipped, for example, with woven stacked packing. The point of entry of the stream (F13) is located between the fifth and the fifteenth theoretical plates starting from the bottom of the distillation column.

In the column of step c), the operating pressure is preferably between 2 and 10 mbar, preferably between 3 and 6 mbar, for example 4 mbar. The pressure drop is preferably from 1 to 10 mbar, preferably from 1 to 8 mbar; for example it is 4 mbar. During step c), the reflux ratio is between 2 and 10, preferably between 2.5 and 6; it is for example 3.

The ratio of the distillation flow rate (flow rate of the stream (F14)) to the feed flow rate (flow rate of the stream (F2) is preferably from 0.5 to 0.95.

The reflux flow rate is preferably from 1.4 to 3 times the feed flow rate; for example, it is twice the feed flow rate.

Preferably:
the flow rate of the stream (F1) is from 150 to 220 kg/h;
the flow rate of the stream (F11) is from 100 to 180 kg/h;
the flow rate of the stream (F2) is from 40 to 55 kg/h;
the flow rate of the stream (F12) is from 3 to 6 kg/h;
the flow rate of the stream (F13) is from 34 to 52 kg/h;
the flow rate of the stream (F14) is from 20 to 60 kg/h.

Preferably, during step c), the temperature at the bottom of the column is between 160° C. and 200° C., in particular between 170° C. and 190° C. Preferably, during step c), the temperature at the top of the column is between 100° C. and 160° C., preferably between 110° C. and 140° C.

The residence time of the vanillin at the bottom of the column of step c) is between 15 minutes and 15 hours, preferably between 30 minutes and 15 hours, more preferably between 7 and 15 hours. in order to reduce this residence time to between 15 minutes and 8 hours and to limit the degradation of the natural vanillin, which is heat-sensitive, it may be advantageous to add a deadweight at the bottom of the column. Deadweights are well known to those skilled in the art; they may in particular consist of glass beads.

In order to perform the distillation of step c), heat can be supplied to the bottom of the column in particular by a falling-film or scraped-film boiler, by a shell-and-tube heat exchanger heated with steam or by a heat-transfer fluid, by means of heating coils fed with steam or by a heat-transfer fluid or by any other equivalent device, preferably by a heat-transfer fluid. Preferably, the energy for the distillation is supplied by a forced-circulation shell-and-tube device or a scraped exchanger.

In one embodiment, the process according to the invention makes it possible to obtain a very pure natural vanillin, in particular having a purity greater than or equal to 99% and preferably containing less than 1000 ppm of vanillyl alcohol. This embodiment can be obtained by adjusting the distillation parameters; in particular the ratio of the distillation flow rate (F14) to the feed flow rate (F2) is then preferably between 0.67 and 0.734.

In another embodiment, the process according to the invention makes it possible to obtain a natural vanillin of lower purity, for example having a purity of 96% to 98.9% and comprising impurities which give the stream of natural vanillin obtained organoleptic properties which are different than those of the very pure natural vanillin and close to those of the vanilla pod. In this embodiment, the final stream of natural vanillin may comprise up to 3% by weight of impurities. Among the impurities are, in the majority, vanillyl alcohol, and the dimers and/or trimers, in particular diphenylmethanes, which can represent up to 1% by weight of the stream, and in the minority, vanillin acid, guaiacol, benzoic acid and biosynthesized organic compounds, which may each be present at up to 500 ppm in the stream. This embodiment can be obtained by adjusting the distillation parameters; in particular the ratio of the distillation flow rate (F14) to the feed flow rate (F2) is then preferably between 0.735 and 0.8.

The invention also relates to a device for implementing this process, comprising:
- a first device (1) for separating the ultralights. in particular the ethyl acetate, from a stream (F1) entering said first device, this first device being in particular a falling-film exchanger or a jacketed reactor;
- a means for connecting the first device to a first distillation column (2) for transferring the stream exiting the first device (F2) to the input of said first column;
- a first distillation column (2) for separating, on the one hand, the lights and, on the other hand, the natural vanillin and the heavies, said first column comprising an input of the stream (F2) originating from the first device and an output at the top of the column comprising the lights (F12), and an output at the bottom of the column comprising the natural vanillin and the heavies (F13);

a means for connecting the first column to a second distillation column (3) for transferring the stream exiting at the bottom of the first column to the input of said second column;

a second distillation column (3) for separating, on the one hand, the natural vanillin and, on the other hand, the heavies, said second column comprising an input of a stream (F13) originating from the first column and an output at the top of the column comprising the natural vanillin (F14), and an output at the bottom of the column comprising the heavies (F15).

The device may also contain a pump (4) for transferring the stream resulting from the first device to the first distillation column.

The device may also contain a condenser connected to one of the outputs of the first device making it possible to recover the ultralights and/or a condenser connected to the column top of the column (2) making it possible to recover the lights and/or a condenser connected to the top of column (3) making it possible to recover the natural vanillin.

The characteristics regarding the first device and the distillation columns are specified above.

Tailing/Topping

In one particular embodiment, the process carried out by continuous distillation comprises the following steps:

a) in a first step, the stream (F1) is treated in order to remove the ultralights (stream (F11)) that it contains and more particularly the ethyl acetate; the resulting stream comprising the natural vanillin, the heavies and the lights is called stream (F2);

b) in a second step, the stream (F2) is fed into a first distillation column, making it possible to recover, at the top of the distillation, a stream (F22) comprising the lights and and the natural vanillin and optionally a low concentration of heavies, and at the bottom of the distillation, a stream (F23) comprising the heavies, in particular vanillyl alcohol, and optionally a low concentration of natural vanillin;

c) the stream (F22) is continuously fed into a second distillation column, making it possible to recover, at the top of the distillation, a stream (F24) comprising the lights and optionally a low concentration of natural vanillin, and at the bottom of the distillation, a stream (F25) comprising the natural vanillin and optionally a low concentration of lights and/or of heavies.

In this embodiment, the term "low concentration" is intended to mean a concentration preferably of at most 10%, preferably of at most 5%, for example of at most 3% by weight relative to the total weight of the fraction.

According to one preferred embodiment of the tailing/topping scheme, at least one part of the stream (F23) is mixed with the stream (F25) so as to be able to vary the final composition of a stream of purified natural vanillin.

Preferably, the stream (F22) at the top of the distillation in step b) comprises the lights, in particular benzoic acid and guaiacol, the natural vanillin and optionally a low concentration of heavies. At the bottom of the distillation (F23) are the heavies, in particular the vanillyl alcohol, and optionally a low concentration of natural vanillin.

Those skilled in the art are perfectly capable of setting the distillation parameters, such as in particular the column diameter, the column height and the packing. The following will simply be mentioned. The size (in particular the diameter) of the distillation columns depends on the stream circulating and on the internal pressure. They will therefore be sized mainly according to the flow rate of mixture to be treated. It will be specified that the column can be packed without distinction with plates or with stacked or woven packing, as is fully known to those skilled in the art. Once the facility has been determined, those skilled in the art adjust the operating parameters of the column.

Preferably, the column of step b) comprises from 10 to 30 theoretical plates, preferably from 15 to 25 theoretical plates. The distillation column of step b) comprises in particular from 4 to 14 theoretical plates for the depletion section and from 6 to 16 theoretical plates for the concentration section.

Preferably. the column of step b) is equipped, for example, with woven stacked packing. The point of entry of the stream (F2) is located between the fifth and the fifteenth theoretical plates starting from the bottom.

In the column of step b), the operating pressure is preferably between 2 and 10 mbar, preferably between 3 and 6 mbar, for example 4 mbar. The pressure drop is preferably from 1 to 10 mbar, preferably from 1 to 8 mbar; for example it is 4 mbar. During step b), the reflux ratio is between 2 and 10, preferably between 2.5 and 6; it is for example 3.

The ratio of the distillation flow rate (flow rate of the stream (F22)) to the feed flow rate (flow rate of the stream (F2)) is preferably from 0.5 to 0.95.

The reflux flow rate is preferably from 1.4 to 3 times the feed flow rate; for example, it is twice the feed flow rate.

Preferably, during step b), the temperature at the bottom of the column is between 160° C. and 200° C., in particular between 170° C. and 190° C. Preferably, during step b), the temperature at the top of the column is between 100° C. and 160° C., preferably between 110° C. and 140° C.

The residence time of the vanillin at the bottom of the column of step b) is between 15 minutes and 15 hours, preferably between 30 minutes and 15 hours, and even more preferably between 7 and 15 hours. In order to reduce this residence time to between 15 minutes and 8 hours and to limit the degradation of the natural vanillin, which is heat-sensitive, it may be advantageous to add a deadweight at the bottom of the column. Deadweights are well known to those skilled in the art; they may in particular consist of glass beads.

In order to perform the distillation of step b), heat can be supplied to the bottom of the column in particular by a falling-film or scraped-film boiler, by a shell-and-tube heat exchanger heated with steam or by a heat-transfer fluid, by means of heating coils fed with steam or by a heat-transfer fluid or by any other equivalent device, preferably by a heat-transfer fluid. Preferably, the energy for the distillation is supplied by a forced-circulation shell-and-tube device or a scraped exchanger.

The stream (F22) at the top of the column at the end of step b) is sent to the distillation column of step c), also called topping column. This stream can be sent in liquid form, the vapors originating from the column of step b) being totally condensed by means of a condenser, or in vapor form, the vapors originating from the column of step b) being partially condensed by means of a partial condenser. Preferably, the stream (F22) is sent to the distillation column of step c) in the vapor phase. This advantageously enables a direct saving of live vapor for the distillation column of step c). Thus, the operating pressure of the distillation column of step b) must be greater than that of the distillation column of step c) and a partial condenser is placed between the distillation column of step b) and that of step c). The partial condenser may be of any type of condenser known to those skilled in the art; it may for example be a condenser of shell-and-tube type.

Preferably, the stream (F24) at the top of the distillation in step c) comprises the lights, in particular benzoic acid and guaiacol, and optionally natural vanillin at low concentration.

Preferably, the distillation column of step c) comprises from 20 to 35 theoretical plates, preferably from 23 to 30 theoretical plates. The distillation column of step b) comprises in particular from 8 to 15 theoretical plates for the concentration section and from 12 to 20 theoretical plates for the depletion section, preferably from 10 to 13 theoretical plates for the concentration section and from 13 to 17 theoretical plates for the depletion section. The distillation column c) may be a distillation column equipped with stacked packing with a height of from 2×2600 mm to 2×3000 mm (2600 to 3000 mm for each of the concentration and depletion sections). The packing of the column is preferably woven packing owing to the very low processing pressures.

In the column of step c), the operating pressure is preferably between 2 and 10 mbar, preferably between 3 and 6 mbar, for example 4 mbar. The pressure drop is preferably from 1 to 10 mbar, preferably from 1 to 8 mbar; for example it is 4 mbar. During step c), the reflux ratio is between 10 and 30, preferably between 15 and 25; it is for example 20. The stream (F22) feed point is selected in a manner known to those skilled in the art, it is in particular selected in such a way as to avoid back-mixing. Preferably, the feed point is at the top of the depletion section.

The ratio of the distillation flow rate (flow rate of the stream (F24)) to the feed flow rate (flow rate of the stream (F2) is preferably from 0.05 to 0.5.

The reflux flow rate is preferably from 1.4 to 3 times the feed flow rate; for example, it is twice the feed flow rate.

Preferably, during step c), the temperature at the bottom of the column is between 100° C. and 160°C., in particular between 120° C. and 150° C. Preferably, during step c), the temperature at the top of the column is between 80° C. and 120° C., preferably between 90° C. and 110° C.

The residence time of the vanillin at the bottom of the column of step a) is between 30 minutes and 5 hours; it is for example 3 hours.

The distillation is initiated by adjusting the flow rate of stream (F22) so as to maintain an approximate temperature of from 100 to 160° C. The temperature difference between the top (vapor temperature) and the bottom (temperature of the liquid) is between 35 and 45° C.

In order to perform the distillation of step a), heat can be supplied to the bottom of the column in particular by a falling-film or scraped-film boiler, by a shell-and-tube heat exchanger heated with steam or by a heat-transfer fluid, by means of heating coils fed with steam or by a heat-transfer fluid or by any other equivalent device, preferably by a heat-transfer fluid. Preferably, the energy for the distillation is supplied by a boiler of falling-film type, a forced-circulation shell-and-tube device or a themosiphon shell-and-tube device.

Preferably:
the flow rate of the stream (F1) is from 150 to 220 kg/h;
the flow rate of the stream (F11) is from 100 to 180 kg/h;
the flow rate of the stream (F2) is from 40 to 55 kg/h;
the flow rate of the stream (F22) is from 33 to 52 kg/h;
the flow rate of the stream (F23) is from 7 to 17 kg/h;
the flow rate of the stream (F25) is from 20 to 60 kg/h.

In one embodiment, the process according to the invention makes it possible to obtain a very pure natural vanillin, in particular having a purity greater than or equal to 99% and preferably containing less than 1000 ppm of vanillyl alcohol. This embodiment can be obtained by adjusting the distillation parameters; in particular the ratio of the distillation flow rate (F24) to the feed flow rate (F2) is then preferably between 0.06 and 0.083.

In another embodiment, the process according to the invention makes it possible to obtain a natural vanillin of lower purity, for example having a purity of 96% to 98.9% and comprising impurities which give the stream of natural vanillin obtained organoleptic properties which are different than those of the very pure natural vanillin and close to those of the vanilla pod. In this embodiment, the final stream of natural vanillin may comprise up to 3% by weight of impurities. Among the impurities are, in the majority, vanillyl alcohol, and the dimers and/or trimers, in particular diphenylmethanes, which can represent up to 1% by weight of the stream, and in the minority, vanillic acid, guaiacol, benzoic acid and biosynthesized organic compounds, which may each be present at up to 500 ppm in the stream. This embodiment can be obtained by adjusting the distillation parameters; in particular the ratio of the distillation flow rate (F24) to the feed flow rate (F2) is then preferably between 0.084 and 0.1.

The invention also relates to a device for implementing this process, comprising:
a first device (1) for separating the ultralights, in particular the ethyl acetate, from a stream (F1) entering said first device, this first device being in particular a falling-film exchanger or a jacketed reactor;
a means for connecting the first device to a first distillation column (5) for transferring the stream (F2) exiting the first device to the input of said first column;
a first distillation column (5) for separating, on the one hand, the lights and the vanillin and, on the other hand, the heavies, said first column comprising an input of the stream (F2) originating from the first device and an output at the top of the column comprising the lights and the natural vanillin (F22), and an output at the bottom of the column comprising the heavies (F23);
a means for connecting the first column to a second distillation column (6) for transferring the stream (F22) exiting at the top of the first column to the input of the second column;
a second distillation column (6) for separating, on the one hand, the natural vanillin and, on the other hand, the lights, said second column comprising an input of a stream (F22) originating from the first column and an output at the top of the column comprising the lights (F24), and an output at the bottom of the column comprising the natural vanillin (F25).

The device may also contain a pump (4) for transferring the stream resulting from the first device to the first distillation column.

The device may also contain a condenser connected to one of the outputs of the first device and making possible to recover the ultralights and/or a condenser connected to the column top of the column (6) making it possible to recover the lights.

In the case where the input stream of the second distillation column is introduced in the vapor phase, the device also comprises a partial condenser connecting the column top of the first column (5) and the feed point of the second column (6).

In the case where the input stream of the second distillation column is introduced in the liquid phase. the device also comprises a condenser connecting the column top of the first column (5) and the feed point of the second column (6).

The characteristics regarding the first device, the condenser and the distillation columns are specified above.

The embodiment comprising the use of a partial condenser allows considerable energy savings to be made, in particular in the context of high production.

Continuous Distillation by Means of a Divided Wall Column (or DWC)

In one embodiment, the process according to the invention is carried out by continuous distillation using a divided wall column.

The process carried out by continuous distillation by means of a divided wall column comprises the following steps:
  a) in a first step, the stream (F1) is treated in order to remove the ultralights (stream (F11)) that it contains and more particularly the ethyl acetate; the resulting stream thus obtained comprising the natural vanillin, the lights and the heavies is called stream (F2);
  b) in a second step, the stream (F2) is fed into a divided wall column which makes it possible to recover, at the top of the column, a stream (F32) comprising the lights and optionally a low concentration of natural vanillin, and at the bottom of the column, a stream (F34) comprising the heavies, and in particular vanillyl alcohol, and optionally a low concentration of natural vanillin, the vanillin being recovered in the form of a stream (F33) by drawing off via a sidestream, it being possible for this stream to optionally comprise a low concentration of lights and/or of heavies.

In this embodiment, the term "low concentration" is intended to mean a concentration preferably of at most 10%, preferably of at most 5%, for example of at most 3% by weight relative to the total weight of the fraction.

The drawing off via a sidestream can be carried out in the liquid phase and/or in the vapor phase. This may be done via any method known to those skilled in the art. For example:
  in the liquid phase, a packing wad can be replaced with an overflow recovery tank;
  in the vapor phase, via a link with a side condenser, the vent pressure of which is in equilibrium with the top pressure.

Advantageously, the vapor-phase drawing off via a sidestream avoids entraining the heavies in the stream of natural vanillin obtained.

Advantageously, the liquid-phase drawing off via a sidestream allows energy to be saved, since the removal of enthalpy is very much less than a vapor-phase drawing off.

The vapor-phase drawing off advantageously makes it possible to increase the purity of the vanillin obtained. The liquid-phase drawing off makes it possible, for its part, advantageously to retain impurities in the stream of final natural vanillin, thus making it possible to obtain different organoleptic properties.

Advantageously, the process according to the invention may comprise two simultaneous drawing off procedures via a sidestream, one liquid-phase drawing off via a sidestream and one vapor-phase drawing off via a sidestream. This makes it possible, in a single distillation step, to collect streams of natural vanillin having different purity and therefore having different organoleptic properties.

In the context of the present invention, the term "divided wall column" is intended to mean a distillation column comprising a vertical internal separation segment separating the column into two half-columns with a geometry and a volume independent of one another, a primary half-column in which the feeding of the stream (F2) takes piece and a secondary half-column in which the drawing off of the stream (F34) takes place, the two half-columns communicating with one another, the separation segment not going from one end to the other of the column.

Preferably, the divided wall column is such that the primary half-column comprises between 18 and 30 theoretical stages, preferably between 25 and 30 theoretical stages, for example 27 theoretical stages, and the secondary half-column comprises between 18 and 25 theoretical stages, preferably between 20 and 25 theoretical stages, for example 23 theoretical stages. Preferably, the primary half-column comprises from 10 to 20 theoretical stages for the depletion section and from 8 to 10 theoretical stages for the concentration section. Preferably, the secondary half-column comprises from 10 to 20 theoretical stages above the point of vapor-phase drawing off via a sidestream and from 10 to 15 theoretical stages below the point of vapor-phase drawing off. The liquid-phase drawing off is 1 to 4 plates below the vapor-phase drawing off.

Preferably, the operating pressure of the divided wall column is between 2 and 10 mbar, preferably between 3 and 6 mbar, for example 4 mbar. The pressure drop must preferably be identical m each of the two half-columns forming the divided wall column; for this, the diameter of each half-column is adjusted. The pressure drop in each half-column is 0.5 to 2.5 mbar.

The reflux ratio in each half-column of the divided wall column, which may be identical or different, is preferably between 2 and 10, preferably between 2.7 and 6.

Preferably, the feeding of the stream (F2) takes place between the tenth and the twentieth theoretical stages of the primary half-column, the plates being counted from bottom to top. The vanillin is drawn off via a sidestream from the divided wall column, preferably between the fourth and the fifteenth theoretical stages of the secondary half-column, the plates being counted from bottom to top.

Preferably, the separation segment comprises an orifice which allows a vanillin-enriched stream to pass from the primary half-column to the secondary half-column. The orifice is preferably at least two theoretical plates above the feed with respect to the primary half-column; it is preferably between 2 and 5 plates above the feed, the plates being counted with respect to the primary half-column. The size of the orifice is determined so as to allow a vanillin-enriched and light-poor stream to pass through; the size of the orifice can be determined by those skilled in the art. It is preferably from 5 to 20 mm. for example from 8 to 15 mm, in particular approximately 10 mm, wide across the width of the separation segment.

The residence time at the bottom of the column is preferably from 30 minutes to 13 hours, for example 8 hours. In order to reduce this residence time to between 1 and 7 hours and to limit the degradation of the natural vanillin, which is heat-sensitive, it may be advantageous to add a deadweight at the bottom of the column. Deadweights are well known to those skilled in the art; they may in particular consist of glass beads.

In order to perform the distillation, heat can be supplied to the bottom of the column in particular by a failing-film or scraped-film boiler, by a shell-and-tube heat exchanger heated with steam or by a heat-transfer fluid, by means of heating coils fed with steam or by a heat-transfer fluid or by any other equivalent device, preferably by a heat-transfer fluid.

Preferably, the ratio of the flow rate of total drawing off via a sidestream (vapor and/or liquid) to the flow rate of stream (F2) is from 0.5 to 0.95.

Preferably:

the flow rate of the stream (F1) is from 150 to 220 kg/h;
the flow rate of the stream (F2) is from 40 to 70 kg/h;
the flow rate of the stream (F32) is from 3 to 7 kg/h;
the flow rate of the stream (F33) in the vapor phase is from 20 to 60 kg/h.

When the column comprises a double vapor and liquid drawing off, the flow rate of the vapor stream is from 35 to 45 kg/h and the flow rate of the liquid stream is from 1.0 to 2.5 kg/h.

In one embodiment, the process according to the invention makes it possible to obtain a very pure natural vanillin, in particular having a purity greater than or equal to 99% and preferably containing less than 1000 ppm of vanillyl alcohol. This embodiment is obtained by drawing off the natural vanillin in vapor form. The ratio of the distillation (F33) flow rate to the feed (F2) flow rate is then preferably between 0.5 and 0.734.

In another embodiment, the process according to the invention makes it possible to obtain a natural vanillin of lower purity, for example having a purity of 96% to 98.9% and comprising impurities which give the stream of natural vain obtained organoleptic properties which are different than those of the very pure natural vanillin and close to those of the vanilla pod. In this embodiment, the final stream of natural vanillin may comprise up to 3% by weight of impurities. Among the impurities are, in the majority, vanillyl alcohol, and the dimers and/or trimers, in particular diphenylmethanes, which can represent up to 1% by weight of the stream, and in the minority, vanillic acid, guaiacol, benzoic acid and biosynthesized organic compounds, which may each be present at up to 500 ppm in the stream. The ratio of the distillation (F33) flow rate to the feed (F2) flow rate is then preferably between 0.736 and 0.76.

The process of the invention also makes it possible to obtain, by means of a single distillation step, very pure vanillin, having a purity greater than or equal to 99%, and vanillin having a purity of 96% to 98.9% by envisioning two drawing off procedures via a sidestream, one vapor-phase drawing off making it possible to obtain vanillin having a purity greater than 99%, and one liquid-phase drawing off making it possible to recover vanillin having a purity of 96% to 98.9%.

The present invention also relates to a device for implementing this process, comprising:
a first device (1) for separating the ultralights, in particular the ethyl acetate, from a stream (F1) entering said first device, this first device being in particular a falling-film exchanger or a jacketed reactor;
a means for connecting the first device to a divided wail distillation column (7) for transferring the stream exiting the first device (F2) to the input of said divided wall column;
a divided wall distillation column (7) for separating the lights, the heavies and the natural vanillin, said divided wall column comprising an input of the stream (F2) originating from the first device and an output at the top of the column comprising lights (F32), an output at the bottom of the column comprising the heavies, and one or two devices for drawing off the natural vanillin via a sidestream (F33).

The device also contains a pump (4) for transferring the stream resulting from the first device to the divided wall column.

The divided wall column comprises an internal segment (8) separating the column into two half-columns (71) and (72). The segment comprises an orifice (9) as described above.

The characteristics regarding the first device and the divided wall column are specified above.

The process by means of a divided wall column is the preferred variant of the invention.

Generally, in the processes of the invention, step a) can be carried out for example by means of a falling-film exchanger or a shelled reactor (or jacketed reactor), preferably a falling-film exchanger.

The term "falling-film evaporator" (also called wetting-film evaporator) is intended to mean an apparatus consisting of a generally cylindrical chamber comprising a bundle of vertical tubes, said tubes being heated externally by circulation of steam in said chamber. The stream (F1) is fed via the upper part and falls onto a distribution system for example with an overflow allowing good distribution of the liquid at the top of the tubes so as to form a liquid film of fine thickness, generally less than 1 mm, preferably between 0.3 and 0.5 mm.

During this pre-step, the operating pressure is preferably atmospheric pressure.

The surface area of the exchanger is preferably from 0.3 to 0.6 $m^2$ for a feed flow rate of approximately 200 kg/h. For a different flow rate, those skilled in the art are capable, by virtue of their general knowledge, of determining the surface area of the exchanger.

The ultralights, in particular the ethyl acetate, can be recovered, using a condenser, for subsequent use.

At the bottom of the falling-film evaporator, a recovery pump makes it possible to send the liquid stream (F2) recovered at the output to the distillation column of step b), also called divided wall column. The stream (F2) corresponds to the stream (F1) substantially or totally free of ultralights. The stream (F2) may optionally contain traces of ultralights that will be trapped in the cold trap of the column of step b).

In a second particular aspect, a subject of the invention is a process for purifying natural vanillin having a purity ranging from 95% to 99% by weight, so as to obtain weakly colored natural vanillin, comprising the following steps:
(a) melting the natural vanillin;
(b) subjecting the molten vanillin derived from step (a) to a vacuum evaporation step;
(c) recovering a condensate of purified natural vanillin. In this second particular aspect, a natural vanillin having a purity ranging from 95% to 99% by weight, i.e. comprising from 95% to 99% by weight of natural vanillin, is used. It may also typically comprise from 1% to 5% by weight of impurities comprising phenolic oligomers. Among the impurities comprising phenolic oligomers, mention may in particular be made of vanillin dialers and trimers.

The natural vanillin used in the process according to the invention has therefore generally been pre-purified in order to achieve the degree of purity of 95% to 99% by weight.

Such a purification may have been carried out by any known method which makes it possible to achieve such a degree of purity, starting from a crude natural vanillin, i.e. one directly derived from biosynthesis. Preferably, the vanillin has been pre-purified by distillation, in particular as described above in the context of the first aspect of the process according to the invention. Where appropriate, an extraction with organic solvent, optionally followed by precipitation or crystallization of the natural vanillin, can be carried out in order to perform such a purification.

Preferably, the second aspect of the process according to the invention uses a natural vanillin obtained by distillation of crude natural vanillin derived from a biosynthesis process.

Preferably, this pre-purification step will have made it possible to remove, inter alia, compounds of which the volatility is higher than that of natural vanillin under the pressure and temperature conditions under consideration. These compounds, which are derived from processes for preparing natural vanillin, may be, inter age, benzoic acid, vanillyl alcohol, guaiacol and a solvent, preferably a food-grade solvent such as ethyl acetate.

The term "volatility" denotes, in a manner known per se, the capacity of a substance to vaporize.

In the second aspect of the process according to the invention, the crude natural vanillin directly derived from biosynthesis typically comprises:

- natural vanillin in a proportion which can range from 5% to 35% by weight, in particular from 10% to 30% by weight;
- vanillyl alcohol in a proportion which can range from 0.05% to 10% by weight, preferably from 0.1% to 5% by weight;
- vanillic acid in a proportion which can range from 0% to 2% by weight, preferably from 0.01% to 0.6% by weight;
- ferulic acid in a proportion which can range from 0% to 2% by weight, preferably from 0.01% to 0.9% by weight;
- guaiacol in a proportion which can range from 0% to 2% by weight, preferably from 0.01% to 0.6% by weight;
- dimers and trimers in a proportion which can range from 0% to 5% by weight, preferably from 0.05% to 5% by weight, more preferably from 0.1% to 5% by weight; the dimers and trimers being compounds with a backbone having respectively two or three phenyl groups, the dimers being advantageously selected from diphenylmethanes;
- various organic compounds which have likewise been biosynthesized (for instance 4-methyl guaiacol, 4-ethyl guaiacol and/or 4-vinyl guaiacol) in a proportion which can range from 0.0% to 5% by weight, preferably from 0.01% to 5% by weight, more preferably from 0.05% to 1% by weight;
- benzoic acid in a proportion which can range from 0% to 10% by weight, preferably from 0.01% to 10% by weight, more preferably from 0.05% to 5% by weight;
- water in a proportion which can range from 0% to 5% by weight, preferably from 0.01% to 5% by weight, more preferably from 0.05% to 3% by weight;
- the remainder to 100% by weight being a food-grade solvent, in particular ethyl acetate.

In the second aspect of the process according to the invention, the biosynthesis process from which the natural vanillin used in the invention is derived preferably confers on this natural vanillin organoleptic properties close to those of the vanilla pod.

Particularly preferably, the second aspect of the process according to the invention uses a natural vanillin having a purity ranging from 96% to 98.9% by weight.

According to another characteristic of the invention, the second aspect of the process according to the invention comprises an additional step (d) consisting of the recovery of a residue comprising phenolic oligomers, such as those described above.

In one preferred embodiment of the second aspect of the process according to the invention, the natural vanillin is melted during step (a) at a temperature ranging from 70 to 110° C. and at atmospheric pressure, more preferentially at a temperature ranging from 75 to 100° C. and at atmospheric pressure.

In the second aspect of the process according to the invention, step (a) is advantageously carried out under an inert gas atmosphere, i.e. which preferably has an oxygen content of less than or equal to 1% by volume. Suitable inert gases are nitrogen and argon, and mixtures thereof.

According to another characteristic of the second aspect of the process according to the invention, evaporation step (b) is advantageously carried out at a pressure ranging from 1 to 10 mbar and at a temperature ranging from 110 to 160° C.

More preferably, evaporation step (b) is carried out at a pressure ranging from 1 to 6 mbar. Equally preferably, evaporation step (b) is carried out at a temperature ranging from 115 to 135° C.

According to one particularly advantageous embodiment of the second aspect of the process according to the invention, step (b) of the invention is carried out in an evaporator. Said evaporator may more particularly be selected from a scraped-film evaporator or a falling-film evaporator. Particularly preferably, step (b) is carried out in a scraped-film evaporator.

Evaporators that can be used for this purpose are thus thin-film evaporators such as falling-film or scraped-film evaporators. Such evaporators are commercially available, from the companies Buss AG, GEA Canzler or Kuhni, and are well known to those skilled in the art. In a particularly preferred variant of the second aspect of the process according to the invention, a short-path scraped-film evaporator, the principle of which is based on a short passage time of the product to be evaporated, is used. The scraped-film evaporator has proved to be particularly suitable for purification by evaporation of natural vanillin, and makes it possible to avoid any degradation of this heat-sensitive product.

The molten natural vanillin derived from step (a) is then introduced into such an evaporator. A thin film of liquid phase, comprising the natural vanillin, is evaporated on a heated surface and the liquid phase comprising phenolic oligomers is scraped by a mechanical means of blade or roll type. Said liquid phase may then be recovered in a dedicated container.

The evaporator makes it possible to recover a gas effluent containing the evaporated vanillin, which is then condensed so as to recover the purified vanillin.

Advantageously, the passage time of the natural vanillin in the evaporator is less than or equal to 15 minutes, preferably less than or equal to 10 minutes, more preferably less than or equal to 5 minutes.

According to one passage of the second aspect of the process according to the invention, the natural vanillin condensate recovered in step (c) has a purity greater than or equal to 99% by weight, preferably greater than or equal to 99.5% by weight.

Advantageously, the condensate of purified natural vanillin, obtained by means of the process according to the invention, in particular the first or second particular aspect, is then directly formed by direct solidification, preferably by spalling, pelletizing or prilling (agglomeration).

One of the preferred techniques for forming the condensate of purified natural vanillin is the technique of spelling on a cylinder or on a belt.

In this technique, the condensate of purified natural vanillin is brought into contact with a metal cylinder or belt at a temperature of 50° C., and then, by scraping the solid film obtained on the cylinder with a knife, the condensate is recovered in the form of flakes.

Another preferred technique is pelletizing, which consists of a process of agglomeration of solid particles by solidification on a pelletizing belt cooled to 10° C. Thus, the condensate of purified natural vanillin is in the form of a dry amorphous solid.

Prilling is also a preferred forming technique. It is a technique well known to those skilled in the art, consisting in spraying the vanillin condensate into a stream of cold air or nitrogen so as to obtain solid beads or agglomerates (prills).

The condensate of purified natural vanillin may also be refined by milling or sieving. The milling operation in particular may be performed in a standard apparatus such as a paddle mill, a pin mill or a granulator.

The process according to the invention has the advantage of making it possible to obtain a very weakly colored vanillin of very high purity (greater than 99% by weight).

In order to characterize the coloration of the vanillin obtained, it can be dissolved in ethanol, at a concentration of 10% by weight.

Thus, the condensate of natural vanillin in ethanolic solution at 10% by weight has a color less than or equal to 200 Hazen, preferably less than or equal to 100 Hazen. The color of the vanillin solution can in particular be measured in accordance with ISO standard 6271 or ASTM standard D1209. A Konica-Minolta CM-5 colorimeter can be used for this purpose.

A subject of the invention is also the vanillin which can be obtained by means of the process according to the invention. Said vanillin is in the form of an amorphous solid of which the color, in ethanolic solution at 10% by weight, is less than or equal to 200 Hazen, preferably less than or equal to 100 Hazen.

The present invention is illustrated in a nonlimiting manner by the following examples.

EXAMPLES

The following examples describe the distillation of a stream of vanillin (F1) comprising 20% by weight of natural vanillin; 4% by weight of heavies (vanillic acid, vanillyl alcohol, ferulic acid, 4-methyl guaiacol, 4-ethyl guaiacol, dimers and trimers, sodium benzoate); 0.5% by weight of water; 2.5% by weight of lights (benzoic add and guaiacol); 73% by weight of ultralights (ethyl acetate).

Example 1

Distillation of the Stream (F1) by Batch Distillation 180 kg of the stream (F1) are fed into the boiler of a distillation column, 700 mm in diameter, equipped with 10 theoretical plates, packed with a woven packing having a surface area of 450 m²/m³. The heat-transfer fluid is fixed at the beginning at 110° C. and the coolant is a Gilotherm oil at 20° C. The column is placed at total reflux for 3 hours. A first fraction comprising ethyl acetate is thus recovered at a flow rate of 15 kg/hour with a reflux of 0.5 for 10 hours. The step of removing the acetate is ended when the operating pressure is 4 mbar for a heat-transfer fluid of 160° C.

A second fraction, comprising the lights and 10% by weight of vanillin, is then recovered at a flow rate of 2.4 kg/hour with a reflux ratio of 100 for a period of 4 hours.

The column is again pieced at total reflux for 1 hour when the temperature at the top of the column reaches 139° C.; for this, the heat-transfer fluid is regulated at 165° C.

A fraction of natural vanillin comprising the natural vanillin having a purity of 98.2% is then recovered at a flow rate of 6.1 kg/hour with a reflux of 30 for a period of 10 hours. The operating pressure is 4 mbar. After 10 h, the distillate flow rate is reduced to 3 kg/hour and the reflux ratio is set at 100. The duration of this operation is 0.5 hour. The distillation is stopped when the temperature at the top reaches 143° C., the load remaining in the concentrate is approximately 9.6 kg and comprises the heavies. The purification yield is equal to 93%.

Example 2

Distillation of the Stream (F1) by Continuous Topping/Tailing Distillation

Figure 1:
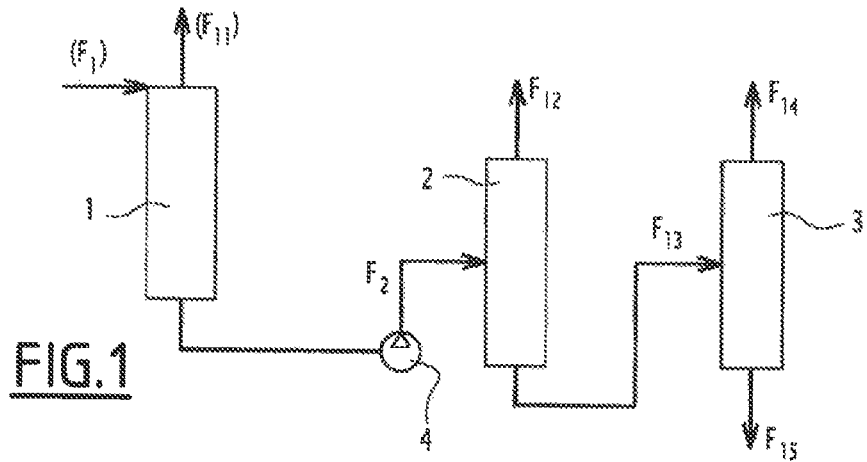
FIG. 1 represents a diagram of continuous topping/tailing distillation of a stream of natural vanillin (F1).

Example 2 refers to FIG. 1.

The stream (F1) is fed at a flow rate of 200 kg/hour at the top of a falling-film exchanger (1). This exchanger makes it possible to remove the ethyl acetate under a stream (F11) at a flow rate of 146 kg/hour. The stream (F11) is sent to a condenser (not represented) for recovery of the ethyl acetate.

A stream (F2) is recovered at the output of the evaporator, which corresponds to the stream (F1) substantially free of ethyl acetate. The traces of ethyl acetate present in the stream (F2) are recovered in the cold trap of a distillation column (2), thus making it possible to protect the column (2). The stream (F2) is sent to a (topping) distillation column (2) by means of a recovery pump (4), in partial recycle mode, at a flow rate of 54 kg/hour. At the top of column (2), a stream (F12) is recovered at a flow rate of 5 kg/hour, comprising benzoic acid, guaiacol and 3% by weight of vanillin. At the bottom of column (2), a stream (F13) is recovered which comprises the heavies and the remaining natural vanillin which is sent to a tailing column (3) at a flow rate of 49 kg/hour. At the top of column (3), a stream (F14) of natural vanillin comprising 3% by weight of heavies, essentially consisting of vanillyl alcohol and of dimers, including diphenylmethane, is recovered at a flow rate of 40 kg/hour. The purity of the vanillin is equal to 97%. The yield of the process is equal to 97%. At the bottom of column (3), a stream (F15) of the heavies and 3% by weight of natural vanillin is recovered at a flow rate of 9 kg/hour.

The characteristics of the device are as follows:
Exchanger (1): Surface area m=0.5 m².
Column (2)
    Equipped with (low-speed woven) stacked packing with a height of 2×2600 mm 24 theoretical plates divided into 11 plates for the concentration section and 13 plates for the depletion section
    Column 4 m in height
    Operating pressure: 4 mbar
    Reflux ratio: 20
    The column is first classified for 5 h with a mixture of vanillin (90% by weight) and benzoic acid (10% by weight). The distillation is then initiated by adjusting the flow rate of stream (F12) so as to maintain an approximate temperature of 140° C. The temperature difference between the top (vapor temperature) and the bottom (temperature of the liquid) is 39.6° C. at 4 mbar. The column is in total reflux for the classification phase.

The energy for the distillation is supplied by a boiler of falling-film type, a forced-circulation shell-and-tube device or a thermosiphon shell-and-tube device.

Column 3
Equipped with woven stacked packing having a surface area of approximately 450 m²/m³ with a height of 2×4560 mm
The feed point is at the mark Z=1500 mm
18 theoretical plates
Diameter of 600 mm
Operating pressure: 4 mbar
The column is placed in total reflux by means of a feedstock of pure vanillin melted beforehand in an oven.
Reflux ratio: 3
Ratio [distillate flow rate]/[feed flow rate] is 0.808
The temperature difference between the top (vapor temperature) and the bottom (temperature of the liquid) is 43° C. at 4 mbar.
The energy for the distillation is supplied by a forced-circulation shell-and-tube device or a scraped exchanger. The pressure on the shell side is 16 bar.

Example 3

Distillation of the Stream (F1) by Continuous Tailing/Topping Distillation

Figure 2:
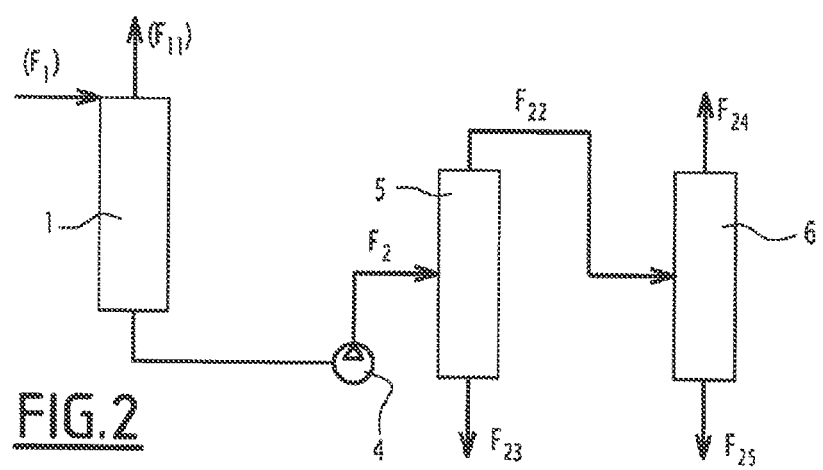
FIG. 2 represents a diagram of continuous tailing/topping distillation of a stream of natural vanillin (F1).

Example 3 refers to FIG. 2.

The stream (F1) is fed at a flow rate of 198.26 kg/hour at the top of a falling-film exchanger (1). This exchanger makes it possible to remove the ethyl acetate under a stream (F11) at a flow rate of 147 kg/hour. The stream (F11) is sent to a condenser (not represented) for recovery of the ethyl acetate.

A stream (F2) is recovered at the output of the evaporator, which corresponds to the stream (F1) substantially free of ethyl acetate. The traces of ethyl acetate present in the stream (F2) are recovered in the cold trap of a distillation column (5), thus making it possible to protect the column (5). The stream (F2) is sent to a (tailing) distillation column (5) by means of a recovery pump (4), in partial recycle mode, at a flow rate of 51.26 kg/hour. At the bottom of column (5), a stream (F23) comprising the heavies and 3% by weight of vanillin is recovered.

At the top of column (5), a stream (F22) comprising the lights, the remaining vanillin and 2.5% by weight of heavies is recovered at a flow rate of 44 kg/hour, and is sent to a topping column (6) at a flow rate of 44 kg/hour. At the top of column (6), a stream (F24) comprising the lights and 3% by weight of vanillin is recovered. At the bottom of column (6), a stream (F25) of natural vanillin comprising the vanillin and 2.5% by weight of heavies is recovered at a flow rate of 38.6 kg/hour. The vanillin obtained has a purity of 99.9% and the purification yield is 98.9%.

The characteristics of the device are as follows:
Exchanger (1): Surface area=0.5 m².
Column (5)
Equipped with woven stacked packing having a surface area of approximately 450 m²/m³ with a height of 2×4560 mm
The feed point is at the mark Z=1500 mm
18 theoretical plates
Diameter of 600 mm
Operating pressure: 4 mbar
Reflux ratio: 3
Ratio [distillate flow rate]/[feed flow rate] is 0.83
The reflux flow rate represents 2.49 times the feed flow rate
The temperature difference between the top (vapor temperature) and the bottom (temperature of the liquid) is 26° C. at 4 mbar.
The energy for the distillation is supplied by a forced-circulation shell-and-tube device or a scraped exchanger. The pressure on the shell side is 12 bar.

Column (6)
Equipped with (low-speed woven) stacked packing with a height of 2×2600 mm
24 theoretical plates divided into 11 plates for the concentration section and 13 plates for the depletion section
Column 4 m in height
Operating pressure: 4 mbar
Reflux ratio: 20
The column is first classified for 5 h with a mixture of vanillin (90% by weight) and benzoic acid (10% by weight). The distillation is then initiated by adjusting the flow rate of stream (F24) so as to maintain an approximate temperature of 140° C., The temperature difference between the top (vapor temperature) and the bottom (temperature of the liquid) is 35° C. at 4 mbar. The column is in total reflux for the classification phase.
The energy for the distillation is supplied by a boiler of falling-film type, a forced-circulation shell-and-tube device or a themosiphon shell-and-tube device. The pressure on the shell side is 10 bar.

An alternative consists in feeding column (6) in the vapor phase: partial condensation via a partial condenser is used for this. This alternative is a direct saving of live vapor for column (6). Column (5) then operates at 5 mbar, column (6) remaining at 4 mbar. in this case, the temperature at the top displays 139° C. The partial condenser comprises an LIC regulating loop which controls the reflux flow rate. The total vapor flow rate arriving at the boiler is controlled by servo-control of the heat load to the boiler by the pressure drop of the column (ΔP=3 mbar). The condenser is a horizontal shell-and-tube device comprising 80 tubes; of ND10 (ND: Nominal Diameter in mm) and of length 1150 mm.

The coolant is a Gilotherm oil at 85° C. and at a flow rate of 533 L/h.

The set liquid height of the LIC is 165 mm. This emergence makes it possible to obtain 44 kg/h of efflux for 176 kg/h of vapor phase which enters the condenser. The tared valve of the condenser vent is regulated at 5 mbar (opening if >5 mbar). The flow rate of live vapor at the input of column (6) is regulated so as to ensure a pressure drop of 3.3 mbar.

Example 4

Figure 3:
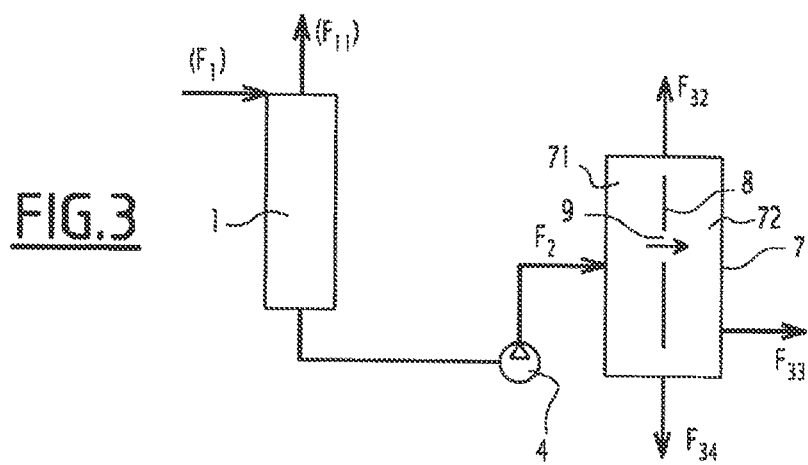
FIG. 3 represents a diagram of continuous distillation in a divided wall column of a stream of natural vanillin (F1).

Distillation of the Stream (F1) on a Divided Wall Column with Vapor-phase Drawing Off Example 4 refers to FIG. 3.

The stream (F1) is fed at a flow rate of 200 kg/hour at the top of a falling-film exchanger (1). This exchanger makes it possible to remove the ethyl acetate under a stream (F11) at a flow rate of 147 kg/hour. The stream (F11) is sent to a condenser (not represented) for recovery of the ethyl acetate.

A stream (F2) is recovered at the output of the evaporator, which corresponds to the stream (F1) substantially free of ethyl acetate. The traces of ethyl acetate present in the stream (F2) are recovered in the cold trap of a distillation column (7), thus making it possible to protect the pump of the column. The stream (F2) is sent to a distillation column (7) at a flow rate of 53 kg/hour. The following are recovered:

- a stream (F32) comprising the lights and 3% by weight of vanillin at a flow rate of 5 kg/hour at the top of the column;
- a stream (F33) by drawing off via a sidestream, comprising vanillin with a purity of 98.9% and 1.1% by weight of heavies essentially consisting of vanillyl alcohol at a flow rate of 39 kg/hour. The yield of the purification process is equal to 96.5%;
- a stream (F34) at the bottom of the column, comprising the heavies and 3% by weight of vanillin at a flow rate of 8 kg/hour.

The characteristics of the device are as follows:
Exchanger (1): Surface area=0.5 m².
Column (7)
  Divided wall column equipped with a dividing wall segment (8) delimiting a primary half-column (71) and a secondary half-column (72)
  stacked packing with a specific surface area of 450 m²/m³ in the primary half-column (71) with a height of 5410 mm and stacked packing in the secondary half-column (72) with a height of 4560 mm
  The primary half-column has 27 stages
  The secondary half-column has 23 stages
  Operating pressure: 4 mbar
  Reflux ratio: 3 in each half-column.
  A passage (9) in the segment (8) at the 3110 mm mark makes it possible to enrich the concentration section of the 2nd half-column. The opening of the passage is a strip which does not exceed 10 mm in width.
  A temperature difference between bottom and top of 74.9° C. when the top temperature is around 116° C.
  The reflux flow rate of the downstream section represents 2.18 times the feed flow rate (F2) and that of the upstream section represents 25% of the feed flow rate (F2).
  The set pressure drop is 1.3 mbar for the column.
  The energy for the distillation is supplied by a boiler of scraped-film type, or a forced-circulation shell-and-tube device.

Example 5

Distillation of the Stream (F1) on a Divided Wall Column by Vapor/Liquid Double Drawing Off Example 5 refers to FIG. 3 to which an additional liquid drawing off point is added.

The stream (F1) is fed at a flow rate of 200 kg/hour at the top of a falling-film exchanger (1). This exchanger makes it possible to remove the ethyl acetate under a stream (F11) at a flow rate of 147 kg/hour. The stream (F11) is sent to a condenser for recovery of the ethyl acetate.

A stream (F2) is recovered at the output of the evaporator, which corresponds to the stream (F1) substantially free of ethyl acetate. The traces of ethyl acetate present in the stream (F2) are recovered in the cold trap of a distillation column (7), thus making it possible to protect the pump of the column. The stream (F2) is sent to a distillation column (7) at a flow rate of 53 kg/hour. The following are recovered:

- a stream (F32) comprising the lights and 3% by weight of vanillin at a flow rate of 5 kg/hour at the top of the column;
- a stream (F33) by vapor-phase drawing off via a sidestream, comprising vanillin with a purity of 99.8% and 0.2% by weight of heavies essentially consisting of vanillyl alcohol at a flow rate of 38.2 kg/hour;
- a stream (F35) (not represented) by liquid-phase drawing off via a sidestream, comprising vanillin with a purity of 98% and 2% by weight of heavies at a flow rate of 1.7 kg/hour;
- a stream (F34) at the bottom of the column, comprising the heavies and 3% by weight of vanillin at a flow rate of 8 kg/hour.

The overall purification yield is 98.5%.
The characteristics of the device are as follows:
Exchanger (1): Surface area=0.5 m².
Column (7)
  Divided wall column equipped with a dividing wall segment (8) delimiting a primary half-column (71) and a secondary half-column (72)
  stacked packing with a specific surface area of 450 m²/m³ in the primary half-column (71) with a height of 5410 mm and stacked packing in the secondary half-column (72) with a height of 4560 mm
  The primary half-column has 27 stages
  The secondary half-column has 23 stages
  Operating pressure: 4 mbar
  Reflux ratio: 3 in each half-column.
  A passage (9) in the segment (8) at the 3110 mm mark makes it possible to enrich the concentration section of the 2nd half-column. The opening of the passage is a strip which does not exceed 10 mm in width.
  The vapor-phase drawing off via a sidestream is located at 1200 mm with respect to the base of the packing bed.
  The liquid-phase drawing off via a sidestream is located 400 mm below the vapor-phase drawing off via a sidestream.
  A temperature difference between bottom and top of 74.9° C. when the top temperature is around 116° C.
  The reflux flow rate of the downstream section represents 2.18 times the feed flow rate (F2) and that of the upstream section represents 25% of the feed flow rate (F2).
  The set pressure drop is 1.3 mbar for the column.
  The energy for the distillation is supplied by a boiler of scraped-film type, or a forced-circulation shell-and-tube device.

Example 6

Purification in a Scraped-film Evaporator (According to the Invention)

10 kg of natural vanillin, having a purity of 98.5% by weight and a coloration of approximately 5 Gardner (according to ASTM standard D1544) in ethanolic solution at 10% by weight, are melted in an oven, under nitrogen, at 95° C. and at atmospheric pressure. The molten natural vanillin is then added to a thermostatted dropping funnel which feeds a short-path scraped-film 0.05 m² evaporator (KDL-5 evaporator sold by the company UIC GmbH) at a temperature of 135° C. and at a pressure of 3 mbar. The rotation speed of the evaporator is 200 revolutions/min and the residence time of the vanillin in the evaporator is 45 seconds. The feed flow rate used is 500 g/h of molten natural vanillin, The natural vanillin vapors are condensed at 100° C. on the internal condenser of the scraped-film evaporator and the liquid condensate is directed to a pelletizing belt cooled to 10° C. The residue comprising phenolic oligomers is discharged into a residue container.

The pellets are recovered and then weighed.

At the end of the process according to the invention, 9.8 kg of purified natural vanillin are obtained, i.e. a yield of 98% by weight, having a purity greater than or equal to 99.5% by weight, and having a color (in ethanolic solution at 10% by weight) equal to 60 Hazen (ISO standard 6271).

Example 7 (Comparative)

The same batch of natural vanillin as in example 6, having a purity of 98.5% by weight, was purified by recrystallization from a water/ethanol mixture (20/80 by weight).

At the end of the purification by recrystallization, purified natural vanillin, having a degree of purity equal to 98.8% by weight, is obtained with a yield of 80% by weight. In ethanolic solution at 10% by weight, it has a coloration of 4 Gardner (according to ASTM standard D1544), i.e. much greater than 500 Hazen.

In fact, the process according to the invention makes it possible to obtain very pure natural vanillin, with a better yield, and especially a much weaker coloration (much whiter vanillin).

The invention claimed is:

1. A natural vanillin having a purity greater than or equal to 96% that is in the form of an amorphous solid of which the color, in ethanolic solution at 10% by weight, is less than or equal to 200 Hazen.

2. A natural vanillin according to claim 1 which can be obtained by means of a process comprising at least one step in which natural vanillin is evaporated.

3. A natural vanillin according to claim 1 having a purity greater than or equal to 98%.

4. A natural vanillin according to claim 3 having a purity greater than or equal to 99% and containing less than 1000 ppm of vanillyl alcohol.

5. A natural vanillin according to claim 1 having a purity of 96% to 98.9% and comprising up to 3% by weight of impurities.

6. A natural vanillin according to claim 5 characterized by organoleptic properties close to the organoleptic properties of vanilla pod.

7. A natural vanillin according claim 1 which is formed by direct solidification.

8. A natural vanillin according to claim 1 which is refined by milling or sieving.

9. A natural vanillin according to claim 2 having a purity greater than or equal to 98%.

10. A natural vanillin according to claim 9 having a purity greater than or equal to 99% and containing less than 1000 ppm of vanillyl alcohol.

11. A natural vanillin according to claim 2 having a purity of 96% to 98.9% and comprising up to 3% by weight of impurities.

12. A natural vanillin according to claim 11 characterized by organoleptic properties close to the organoleptic properties of vanilla pod.

13. A natural vanillin having a purity greater than or equal to 96% that is in the form of an amorphous solid of which the color, in ethanolic solution at 10% by weight, is less than or equal to 100 Hazen.

14. A natural vanillin according to claim 1 having a purity greater than or equal to 99%.

15. A natural vanillin according to claim 1 which is formed by spalling, pelletizing or prilling, more preferably by spalling on a cylinder or on a belt.

16. A natural vanillin according claim 1 which is formed by spalling on a cylinder or on a belt.

17. A natural vanillin according to claim 2 having a purity greater than or equal to 99%.

18. A natural vanillin according to claim 13 having a purity greater than or equal to 99% and containing less than 1000 ppm of vanillyl alcohol.

19. A natural vanillin according to claim 13 having a purity of 96% to 98.9% and comprising up to 3% by weight of impurities.

20. A natural vanillin according to claim 13 characterized by organoleptic properties close to the organoleptic properties of vanilla pod.

* * * * *